US010603277B2

(12) United States Patent
Dhuppad et al.

(10) Patent No.: US 10,603,277 B2
(45) Date of Patent: Mar. 31, 2020

(54) NANOPARTICULATE FORMULATION COMPRISING A TRPA1 ANTAGONIST

(71) Applicant: GLENMARK PHARMACEUTICALS S.A., La Chaux-de-Fonds (CH)

(72) Inventors: Ulhas Rameshchandra Dhuppad, Nashik (IN); Sunil Sudhakar Chaudhari, Nashik (IN); Suresh Mahadev Rajurkar, Nashik (IN); Nilesh Jayantilal Jain, Nashik (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

(21) Appl. No.: 14/310,447

(22) Filed: Jun. 20, 2014

(65) Prior Publication Data

US 2014/0377358 A1 Dec. 25, 2014

(30) Foreign Application Priority Data

Jun. 20, 2013 (IN) ......................... 2090/MUM/2013

(51) Int. Cl.
*A61K 9/14* (2006.01)
*A61K 9/16* (2006.01)
*A61K 9/51* (2006.01)
*A61K 31/519* (2006.01)
*A61K 9/20* (2006.01)

(52) U.S. Cl.
CPC .............. *A61K 9/14* (2013.01); *A61K 9/1676* (2013.01); *A61K 9/5123* (2013.01); *A61K 9/5138* (2013.01); *A61K 9/5146* (2013.01); *A61K 9/5192* (2013.01); *A61K 31/519* (2013.01); *A61K 9/2081* (2013.01)

(58) Field of Classification Search
CPC ...... A61K 9/2081; A61K 9/5192; A61K 9/14; A61K 9/5146; A61K 9/1676; A61K 9/5138; A61K 31/519
See application file for complete search history.

(56) References Cited

U.S. PATENT DOCUMENTS

| | | | | |
|---|---|---|---|---|
| 5,145,684 | A | 9/1992 | Liversidge et al. | |
| 7,998,507 | B2 | 8/2011 | Bosch et al. | |
| 8,258,132 | B2 | 9/2012 | Bosch et al. | |
| 8,614,201 | B2 | 12/2013 | Berthelot et al. | |
| 8,771,740 | B2 | 7/2014 | Kerkhof | |
| 2007/0065374 | A1* | 3/2007 | Liversidge et al. | 424/46 |
| 2008/0254114 | A1 | 10/2008 | Jenkins et al. | |
| 2012/0010223 | A1 | 1/2012 | Kumar et al. | |
| 2012/0196894 | A1 | 8/2012 | Bilodeau et al. | |
| 2013/0289054 | A1 | 10/2013 | Kumar et al. | |
| 2015/0111038 | A1 | 4/2015 | Kadam et al. | |

FOREIGN PATENT DOCUMENTS

| | | | |
|---|---|---|---|
| WO | 99/39700 | A1 | 8/1999 |
| WO | WO 2012176105 | * | 12/2012 |

OTHER PUBLICATIONS

International Search Report dated Oct. 9, 2014, for corresponding International Patent Application No. PCT/IB2014/062462.
International Preliminary Report on Patentability dated Dec. 22, 2015, for corresponding International Patent Application No. PCT/IB2014/062462.
Notice of Reasons for Rejection mailed by the Japanese Patent Office dated Sep. 13, 2016, for corresponding Patent Application No. JP 2016-520798.

* cited by examiner

*Primary Examiner* — Johann R Richter
*Assistant Examiner* — Genevieve S Alley
(74) *Attorney, Agent, or Firm* — Pergament & Cepeda LLP; Milagros A. Cepeda; Edward D. Pergament

(57) ABSTRACT

The present invention relates to a nanoparticulate formulation comprising a transient receptor potential ankyrin-1 receptor ("TRPA1") antagonist. Particularly, the present invention relates to a nanoparticulate formulation comprising a thienopyrimidinedione derivative as a TRPA1 antagonist and a surface stabilizer; a process for preparing such formulation; and its use in treating a respiratory disorder or pain in a subject.

5 Claims, No Drawings

NANOPARTICULATE FORMULATION COMPRISING A TRPA1 ANTAGONIST

PRIORITY DOCUMENT

This patent application claims priority to Indian Provisional Patent Application number 2090/MUM/2013 filed on Jun. 20, 2013, the contents of which are incorporated by reference herein.

TECHNICAL FIELD OF THE INVENTION

The present invention relates to a nanoparticulate formulation comprising a transient receptor potential ankyrin-1 receptor ("TRPA1") antagonist. Particularly, the present invention relates to a nanoparticulate formulation comprising a thienopyrimidinedione derivative as a TRPA1 antagonist and a surface stabilizer; a process for preparing such formulation; and; its use in treating a respiratory disorder or pain in a subject.

BACKGROUND OF THE INVENTION

Respiratory disorders related to airway inflammation include a number of severe lung diseases including asthma and chronic obstructive pulmonary disease ("COPD"). The airways of asthmatic patients are infiltrated by inflammatory leukocytes, of which the eosinophil is believed to be the most prominent component. Inflammatory sensitization of airway neurons is believed to increase nasal and cough sensitivity, heighten the sense of irritation, and promote fluid secretion, airway narrowing, and bronchoconstriction.

Various classes of drugs are currently being used for the treatment and/or prophylaxis of respiratory disorders like asthma and COPD. Some of the classes of such drugs are leukotriene receptor antagonists, $\beta_2$-adrenergic agonists, anticholinergics and corticosteroids.

The TRPA1 receptor activation in the airways by noxious stimuli, including cold temperatures (generally, less than about 17° C.), pungent natural compounds (e.g., mustard, cinnamon and garlic), tobacco smoke, tear gas and environmental irritants, is supposed to be one of the mechanisms for neurogenic inflammation in the airways. Neurogenic inflammation is an important component of chronic airway diseases like COPD and asthma. Thus, TRPA1 antagonists are believed to play a role in the treatment of chronic airway diseases like COPD and asthma.

TRPA1 receptors are also found at the ends of sensory nerves and their activation results in painful sensations. Thus, TRPA1 antagonists are also believed to play a role in the treatment of pain.

PCT Application Publication Nos. WO 2011/043954, WO 2010/109334, WO 2010/109328 and WO 2010/141805 describe various transient receptor potential ("TRP") receptor modulators.

U.S. Pat. Nos. 5,145,684 and 7,998,507, and PCT Application Publication No. WO2003/049718 disclose nanoparticulate compositions.

There is a need for new, improved formulations of TRPA1 antagonists and methods of making and using such formulations.

SUMMARY OF THE INVENTION

The present invention relates to a nanoparticulate formulation comprising a TRPA1 antagonist.

Co-assigned PCT Publication No. WO 2010/109334 ("the '334 application") discloses, as TRPA1 modulators, certain thienopyrimidinedione derivative compounds.

Inter alia, the '334 application discloses a compound N-{4-[2,4-difluoro-3-(trifluoromethyl)phenyl]-1,3-thiazol-2-yl}-2-(1,3-dimethyl-2,4-dioxo-1,2,3,4-tetrahydrothieno [2,3-d]pyrimidin-5-yl)acetamide (hereinafter, "Compound I") having structural formula:

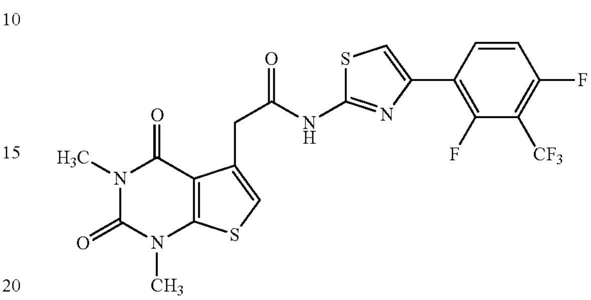

or its pharmaceutically acceptable salt, or other derivative. All stereoisomers of the Compound I including enantiomers and diastereomers are separately contemplated.

In one embodiment, the present invention relates to a nanoparticulate formulation comprising Compound I or its salt and a surface stabilizer, said formulation having an effective average particle size in the range from about 20 nm to about 1000 nm.

Preferably, the salt of Compound I includes sodium salt or potassium salt.

The surface stabilizer as contemplated herein includes a polymer and a surfactant. In the context of present invention, the surfactant includes, but is not limited to, poloxamer, polyoxyethylene sorbitan esters (known as Polysorbate® or Tween®), polyethoxylated castor oil (known as Cremophor), glycerol monostearate, phospholipids, benzalkonium chloride, triethanolamine, sodium lauryl sulfate, docusate sodium, Vitamin E TPGS, soya lecithin, and the like; whereas the polymer includes, but is not limited to, polyvinyl pyrrolidone, copovidone, hydroxypropyl cellulose, hydroxyethyl cellulose, hydroxypropylmethyl cellulose polyethylene glycol, natural gums, and the like.

In an embodiment, the present invention relates to a nanoparticulate formulation comprising Compound I or its salt and a surface stabilizer selected from a polymer or a surfactant, said formulation having an effective average particle size in the range from about 20 nm to about 1000 nm.

In one aspect of the above embodiment, the surface stabilizer is a polymer selected from one or more of polyvinyl pyrrolidone, copovidone, hydroxypropyl cellulose, hydroxyethyl cellulose, hydroxypropylmethyl cellulose, polyethylene glycol and natural gums.

The weight ratio of the compound I or its pharmaceutically acceptable salt to the polymer ranges from about 1:0.1 to about 1:100, or from about 1:0.5 to about 1:50.

In another aspect of the above embodiment the surface stabilizer is a surfactant selected from one or more of poloxamer, polyoxyethylene sorbitan esters, polyethoxylated castor oil, glycerol monostearate, phospholipids, benzalkonium chloride, triethanolamine, sodium lauryl sulfate, docusate sodium, Vitamin E TPGS and soya lecithin.

The weight ratio of the compound I or its pharmaceutically acceptable salt to the surfactant ranges from about 1:0.1 to about 1:100 or from about 1:0.5 to about 1:50.

In one embodiment, the present invention relates to a nanoparticulate formulation comprising particles of Compound I or its salt and a surface stabilizer selected from a polymer and/or a surfactant, said formulation having an effective average particle size in the range from about 30 nm to about 800 nm.

In one aspect of the above embodiment the effective average particle size is in the range from about 50 nm to about 600 nm.

In one aspect of the above embodiment the compound I is in the form of potassium salt.

In another aspect of this embodiment, the nanoparticulate formulation of the present invention has $D_{10}$ value in the range from about 10 nm to about 300 nm, or preferably from about 20 nm to about 200 nm. In another aspect of this embodiment, the nanoparticulate formulation of the present invention has $D_{80}$ value in the range from about 50 nm to about 1000 nm, or preferably from about 70 nm to about 800 nm.

In yet another aspect of this embodiment the effective average particle size is in the range from about 70 nm to about 500 nm.

In yet another aspect of this embodiment the effective average particle size is in the range from about 100 nm to about 400 nm.

In a further aspect of this embodiment, the polymer is selected from one or more of polyvinyl pyrrolidone, copovidone, hydroxypropyl cellulose, hydroxyethyl cellulose, hydroxypropylmethyl cellulose, polyethylene glycol and natural gums. The weight ratio of the compound I or its pharmaceutically acceptable salt to the polymer ranges from about 1:0.1 to about 1:50 or from about 1:1 to about 1:10.

In a still further aspect of this embodiment, the surfactant is selected from one or more of poloxamer, polyoxyethylene sorbitan esters, polyethoxylated castor oil, glycerol monostearate, phospholipids, benzalkonium chloride, triethanolamine, sodium lauryl sulfate, docusate sodium, Vitamin E TPGS and soya lecithin. The weight ratio of the compound I or its pharmaceutically acceptable salt to the surfactant ranges from about 1:0.05 to about 1:50 or from about 1:0.5 to about 1:10.

In one embodiment the present invention related to a nanoparticulate formulation comprising Compound I potassium salt, copovidone, sodium lauryl sulphate or polyethylene glycol and poloxamer, said formulation having an effective average particle size in the range from about 70 nm to about 500 nm.

In one aspect of this embodiment, the effective average particle size is in the range from about 100 nm to about 400 nm.

In another embodiment the present invention related to a nanoparticulate formulation comprising Compound I potassium salt, copovidone, sodium lauryl sulphate or polyethylene glycol and poloxamer are present in a weight ratio of about 1:4:0.5:1, said formulation having an effective average particle size in the range from about 70 nm to about 500 nm.

In one aspect of this embodiment, the effective average particle size is in the range from about 100 nm to about 400 nm.

The nanoparticulate formulation of the present invention can be converted into a suitable pharmaceutical composition which includes, but not limited to dispersion, gel, aerosol, ointment, cream, lotion, paste, spray, film, patch, tablets, capsules, powder, granules, dry syrup, syrup and parenteral preparations such as intravenous, intra-arterial, intramuscular, intra-articular, and subcutaneous injections.

In a preferred embodiment nanoparticulate formulation of the present invention is in the form of a dispersion, liquid suspension, semi-solid suspension, or powder.

In one embodiment the present invention relates to a pharmaceutical composition comprising the nanoparticulate formulation of the invention and a pharmaceutically acceptable excipient.

In an embodiment, the present invention also relates to a pharmaceutical composition that includes: a nanoparticulate formulation comprising particles of Compound I or its salt and a surface stabilizer and a pharmaceutically acceptable excipient, said formulation having an effective average particle size in the range from about 20 nm to about 1000 nm.

The nanoparticulate formulation of the present invention can be administered as such, or alternately, it can be further converted into a suitable pharmaceutical composition such as solid, liquid or semi-solid preparation for ease of administration. The nanoparticulate formulation or its pharmaceutical composition can be administered by appropriate route which includes, but is not limited to, oral, pulmonary, rectal, ophthalmic, parenteral, intravaginal, local, buccal, nasal or topical route. Preferably, the nanoparticulate formulation or its pharmaceutical composition of the present invention is suitable for oral administration.

In one embodiment the present invention relates to a pharmaceutical composition comprising the nanoparticulate formulation of the invention and a pharmaceutically acceptable excipient wherein the composition is an immediate release composition suitable for oral administration.

In one embodiment the present invention relates to a pharmaceutical composition comprising the nanoparticulate formulation of the invention and a pharmaceutically acceptable excipient wherein the composition is an extended release or a delayed release composition suitable for oral administration.

In one embodiment the present invention relates to a process for preparation of a nanoparticulate formulation comprising Compound I or its salt and a surface stabilizer, the process comprising the steps of:

a) mixing Compound I or its salt with the surface stabilizer to form a mixture; and;

b) reducing the particle size of the mixture.

In yet another embodiment the present invention relates to a process for preparation of a nanoparticulate formulation comprising Compound I or its salt and a surface stabilizer, the process comprising the steps of:

a) reducing the particle size of the Compound I or its salt; and;

b) mixing said Compound I or its salt with the surface stabilizer.

The present invention also relates to a method of treating a respiratory disorder or pain in a subject, the method comprising administering to the subject the nanoparticulate formulation (or pharmaceutical composition containing the nanoparticulate formulation) as described herein.

In one embodiment the present invention relates to use of Compound I or its salt and a surface stabilizer in the preparation of a nanoparticulate formulation for treatment of a respiratory disorder or pain in a subject, said formulation having an effective average particle size in the range from about 20 nm to about 1000 nm.

In aspect of this embodiment, the effective average particle size is in the range from about 30 nm to about 800 nm, or from about 50 nm to 600 nm, or from about 70 nm to about 500 nm, or from about 100 nm to 400 nm.

DETAILED DESCRIPTION OF THE INVENTION

The present invention relates to a nanoparticulate formulation comprising a TRPA1 antagonist.

Co-assigned PCT Publication No. WO 2010/109334 ("the '334 application") discloses, as TRPA1 modulators, certain thienopyrimidinedione derivative compounds.

Inter alia, the '334 application discloses a compound N-{4-[2,4-difluoro-3-(trifluoromethyl)phenyl]-1,3-thiazol-2-yl}-2-(1,3-dimethyl-2,4-dioxo-1,2,3,4-tetrahydrothieno [2,3-d]pyrimidin-5-yl)acetamide (hereinafter, "Compound I") having structural formula:

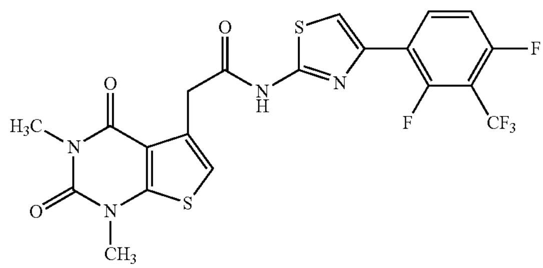 [SMILES: Cn1c(=O)c2c(CC(=O)Nc3nc(-c4ccc(F)c(C(F)(F)F)c4F)cs3)csc2n(C)c1=O]

or its pharmaceutically acceptable salt, or other derivative. All stereoisomers of the Compound I including enantiomers and diastereomers are separately contemplated.

The terms used herein are defined as follows. If a definition set forth in the present application and a definition set forth earlier in a provisional application from which priority is claimed are in conflict, the definition in the present application shall control the meaning of the terms.

The term "active ingredient" (used interchangeably with "active" or "active substance" or "drug") as used herein refers to a TRPA1 antagonist or its pharmaceutically acceptable salt or other derivative. Preferably, the TRPA1 antagonist is Compound I or its pharmaceutically acceptable salt or other derivative. All stereoisomers of the Compound I including enantiomers and diastereomers are separately contemplated.

By "salt" or "pharmaceutically acceptable salt", it is meant those salts and esters which are, within the scope of sound medical judgment, suitable for use in contact with the tissues of humans and lower animals without undue toxicity, irritation, and allergic response, commensurate with reasonable benefit to risk ratio, and effective for their intended use. Representative acid additions salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include the sodium, calcium, potassium and magnesium salts. Preferably, the salt of Compound I includes sodium salt or potassium salt.

The term "surface stabilizer" as used herein includes the agents which associate with the surface of particles of the TRPA1 antagonist, but do not chemically bond to or interact with it. Surface stabilizer generally provides steric and ionic barrier to prevent agglomeration of the particles.

The surface stabilizer as contemplated herein includes polymer and surfactant. In the context of present invention, the polymer includes, but is not limited to one or more of, cellulose derivatives, such as hydroxypropyl methyl cellulose, hydroxypropyl cellulose, methyl cellulose, carboxymethyl cellulose sodium or calcium salt, hydroxylethyl cellulose, polyvinyl pyrrolidone, copovidone, carbopols, copolymers of polyvinyl pyrrolidone, polyoxyethylene alkyl ether, polyethylene glycol, co-block polymers of ethylene oxide and propylene oxide (Poloxamer®, Pluronic®), poly methacrylate derivatives, polyvinyl alcohol, polyvinyl alcohol derivatives and polyethylene glycol derivatives, such as macrogol glycerol stearate, natural gums like xanthan gum, locust bean gum, alginic acid, carrageenan, sodium alginate and the like. Preferably, the polymer includes polyvinyl pyrrolidone, copovidone, hydroxypropyl cellulose, hydroxyethyl cellulose, hydroxypropylmethyl cellulose, polyethylene glycol, Magnesium aluminum silicate, copovidone, natural gums, and the like.

Typically, the surfactant includes, but is not limited to one or more of poloxamer, polyoxyethylene sorbitan esters (known as Polysorbate® or Tween®), polyethoxylated castor oil (Cremophor®), methyl glucose sesquistearate, PEG-20 methyl glucoside sesquistearate, caprylocaproyl macrogol-8 glycerides, lauroyl macrogol-32-glycerides Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 glyceryl monostearate, sucrose monostearate, sucrose polystearates, polyglyceryl 10 stearate, polyglyceryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, steareth-2, PEG-5 soya sterol oil, PEG-10 soya sterol oil, diethanolamine cetyl phosphate, sorbitan monostearate, diethyleneglycol monostearate, glyceryl monostearate, sodium stearyl sulfate, benzalkonium chloride, docusate sodium, triethanolamine, phospholipids and the like. Preferably, the surfactant includes polyoxyethylene sorbitan esters (known as Polysorbate® or Tween®), polyethoxylated castor oil (known as Cremophor®), glycerol monostearate, phospholipids, benzalkonium chloride, triethanolamine, sodium lauryl sulfate, docusate sodium, Vitamin E TPGS, soya lecithin, and the like. Preferrably the surfactant includes, but is not limited to, poloxamer, polyoxyethylene sorbitan esters (known as Polysorbate® or Tween®), polyethoxylated castor oil (known as Cremophor®), glycerol monostearate, phospholipids, benzalkonium chloride, triethanolamine, sodium lauryl sulfate, docusate sodium, Vitamin E TPGS, soya lecithin, and the like.

The "nanoparticulate formulation" in the context of present invention refers to a pharmaceutical dispersion wherein drug particles are dispersed in a solvent, and having an effective average particle size of less than about 1000 nm.

As used herein, the term "average particle size" (or synonymously, "mean particle size") refers to the distribution of particles, wherein about 50 volume percent of all the particles measured have a size less than the defined average particle size value. This can be identified by the term "$D_{50}$" or "d (0.5)".

As used herein, the term "$D_{10}$" refers to the distribution of particles; wherein about 10 volume percent of all the particles measured have a size less than the defined particle size value. This can be identified by the term "d (0.1)" as well. Similarly, as used herein, the term "$D_{80}$" refers to the distribution of particles; wherein about 80 volume percent of all the particles measured have a size less than the defined particle size value. This can be identified by the term or "d (0.8)" as well. On similar lines, as used herein, the term "$D_{90}$" refers to the distribution of particles; wherein about 90 volume percent of all the particles measured have a size less than the defined particle size value. This can be identified by the term or "d (0.9)" as well.

The particle size can be measured using various techniques like laser diffraction, photon correlation spectroscopy (PCS) and Coulter's principle. When PCS is used as the method of determining particle size, the average particle size is the Z-average particle diameter known to those skilled in the art. Typically, instruments like ZETASIZER® 3000 HS (Malvern® Instruments Ltd., Malvern, United Kingdom), NICOMP388™ ZLS system (PSS-Nicomp Particle Sizing Systems, Santa Barbara, Calif., USA), or Coulter Counter are generally used to determine the mean particle size. Preferably, Mastersizer 2000 (Malvern® Instruments Ltd., Malvern, United Kingdom) is used to determine the particle size of the particles.

By "an effective average particle size in the range from about 20 nm to about 1000 nm" it is meant that at least 50% of the total particles of Compound I or its salt have an average particle size in the range from about 20 nm to about 1000 nm when measured by the techniques mentioned herein. It is preferred that at least about 80% or at least about 90% of the particles have a particle size less than the effective average size, e.g., 1000 nm.

In an embodiment, the present invention relates to a nanoparticulate formulation comprising Compound I or its salt and a surface stabilizer, said formulation having an effective average particle size in the range from about 20 nm to about 1000 nm.

In an embodiment, the present invention relates to a nanoparticulate formulation comprising particles of Compound I or its salt and a surface stabilizer, said formulation having an effective average particle size in the range from about 30 nm to about 800 nm.

In one aspect of this embodiment an effective average particle size is in the range from about 50 nm to about 600 nm.

In a preferred embodiment, the present invention provides a nanoparticulate formulation comprising particles of Compound I potassium salt and a surface stabilizer selected from a polymer and/or a surfactant, said formulation having an effective average particle size in the range from about 30 nm to about 800 nm and $D_{80}$ value of said particles is in the range from about 50 nm to about 1000 nm or from about 70 nm to about 1000 nm.

In one aspect of this embodiment an effective average particle size is in the range from about 50 nm to about 600 nm.

In another embodiment, the present invention also provides a nanoparticulate formulation comprising particles of Compound I potassium salt and a surface stabilizer that includes copovidone, poloxamer sodium lauryl sulfate and/or polyethylene glycol, wherein said formulation having an effective average particle size in the range from about 20 nm to about 1000 nm or from about 30 nm to about 800 nm or from about 50 nm to about 600 nm.

In another embodiment, the present invention also provides a nanoparticulate formulation comprising particles of Compound I potassium salt and a surface stabilizer that includes copovidone, poloxamer sodium lauryl sulfate and/or polyethylene glycol, said composition having an effective average particle size in the range from about 70 nm to about 500 nm or from about 100 nm to about 400 nm.

The weight ratio of the Compound I or its pharmaceutically acceptable salt to the surface stabilizer ranges from about 0.01:100 to about 100:0.01 or from about 0.1:100 to about 100:0.1 respectively.

In an embodiment, the present invention relates to a nanoparticulate formulation comprising Compound I or its salt and a surface stabilizer selected from a polymer or a surfactant, said formulation having an effective average particle size in the range from about 20 nm to about 1000 nm.

In one aspect of the above embodiment the surface stabilizer is polymer is selected from one or more of polyvinyl pyrrolidone, copovidone, hydroxypropyl cellulose, hydroxyethyl cellulose, hydroxypropylmethyl cellulose, polyethylene glycol and natural gums.

The weight ratio of the Compound I or its pharmaceutically acceptable salt to the polymer ranges from about 1:0.1 to about 1:100 or from about 1:0.5 to about 1:50.

In another aspect of the above embodiment the surface stabilizer is a surfactant is selected from one or more of poloxamer, polyoxyethylene sorbitan esters, polyethoxylated castor oil, glycerol monostearate, phospholipids, benzalkonium chloride, triethanolamine, sodium lauryl sulfate, docusate sodium, Vitamin E TPGS and soya lecithin.

The weight ratio of the Compound I or its pharmaceutically acceptable salt to the surfactant ranges from about 1:0.1 to about 1:100 or from about 1:0.5 to about 1:50.

In one embodiment, the present invention relates to a nanoparticulate formulation comprising particles of Compound I or its salt and a surface stabilizer selected from a polymer and/or a surfactant, said formulation having an effective average particle size in the range from about 30 nm to about 800 nm.

In one aspect of the above embodiment the effective average particle size is in the range from about 50 nm to about 600 nm. In one aspect of the above embodiment, the compound is in the form of potassium salt.

In another aspect of this embodiment, the nanoparticulate formulation of the present invention has $D_{10}$ value in the range from about 10 nm to about 300 nm, or preferably from about 20 nm to about 200 nm. In another aspect of this embodiment, the nanoparticulate formulation of the present invention has $D_{80}$ value in the range from about 50 nm to about 1000 nm, or preferably from about 70 nm to about 800 nm.

In yet another aspect of this embodiment, the effective average particle size is in the range from about 70 nm to about 500 nm or from about 100 nm to about 400 nm.

In a further aspect of this aspect, the polymer is selected from one or more of polyvinyl pyrrolidone, copovidone, hydroxypropyl cellulose, hydroxyethyl cellulose, hydroxypropylmethyl cellulose, polyethylene glycol and natural gums. The weight ratio of the Compound I or its pharmaceutically acceptable salt to the polymer ranges from about 1:0.1 to about 1:50 or from about 1:1 to about 1:10.

In a still further aspect of this aspect, the surfactant is selected from one or more of poloxamer, polyoxyethylene sorbitan esters, polyethoxylated castor oil, glycerol monostearate, phospholipids, benzalkonium chloride, triethanolamine, sodium lauryl sulfate, docusate sodium, Vitamin E TPGS and soya lecithin. The weight ratio of the Compound I or its pharmaceutically acceptable salt to the surfactant ranges from about 1:0.05 to about 1:50 or from about 1:0.5 to about 1:10.

In one embodiment the present invention related to a nanoparticulate formulation comprising Compound I potassium salt, copovidone, sodium lauryl sulphate or polyethylene glycol and poloxamer, said formulation having an effective average particle size in the range from about 70 nm to about 500 nm.

In one aspect of this embodiment, the effective average particle size is in the range from about 100 nm to about 400 nm.

In another embodiment the present invention related to a nanoparticulate formulation comprising Compound I potassium salt, copovidone, sodium lauryl sulphate or polyethylene glycol and poloxamer are present in a weight ratio of about 1:4:0.5:1, said formulation having an effective average particle size in the range from about 70 nm to about 500 nm.

In one aspect of this embodiment, the effective average particle size is in the range from about 100 nm to about 400 nm.

The nanoparticulate formulation of the present invention can be converted into a suitable pharmaceutical composition which includes, but not limited to dispersion, gel, aerosol, ointment, cream, lotion, paste, spray, film, patch, tablets, capsules, powder, granules, dry syrup, syrup and parenteral preparations such as intravenous, intra-arterial, intramuscular, intra-articular, and subcutaneous injections.

In a preferred embodiment nanoparticulate formulation of the present invention is in the form of a dispersion, liquid suspension, semi-solid suspension, or powder.

The nanoparticulate formulation of the present invention can be administered as such, or alternately, it can be further converted into a suitable pharmaceutical composition such as solid, liquid or semi-solid preparation for ease of administration. The pharmaceutical composition may be prepared by conventional methods known in the art.

In one embodiment the present invention relates to a pharmaceutical composition comprising the nanoparticulate formulation of the invention and a pharmaceutically acceptable excipient.

By "pharmaceutically acceptable excipient" it is meant any of the components of a formulation or pharmaceutical composition other than the active ingredient, and which are approved by regulatory authorities or are generally regarded as safe for human or animal use.

Pharmaceutically acceptable excipient, which includes, but not limited to one or more of diluents, glidants and lubricants, preservatives, buffering agents, chelating agents, polymers, opacifiers, colorants, gelling agents/viscosifying agents, antioxidants, solvents and the like.

Non-limiting examples of diluents includes one or more of microcrystalline cellulose, silicified microcrystalline cellulose (e.g., Prosolv®), microfine cellulose, lactose, starch, pregelatinized starch, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide and the like; cores/beads comprising insoluble inert materials like glass particles/beads or silicon dioxide, calcium phosphate dihydrate, dicalcium phosphate, calcium sulfate dihydrate, cellulose derivatives; soluble cores such as sugar spheres of sugars like dextrose, mannitol, sorbitol, or sucrose; insoluble inert plastic materials such as spherical or nearly spherical core beads of polyvinyl chloride, polystyrene or any other pharmaceutically acceptable insoluble synthetic polymeric material, acacia, guar gum, alginic acid, dextrin, maltodextrin, methylcellulose, ethyl cellulose, hydroxyethyl cellulose, hydroxypropyl cellulose (e.g., Klucel®), low substituted hydroxypropyl cellulose, hydroxypropyl methylcellulose (e.g., Methocer®), carboxymethyl cellulose sodium, povidone (various grades of Kollidon®, Plasdone®), carboxymethyl cellulose calcium, croscarmellose sodium, (e.g., Ac-Di-Sol®, Primellose®), crospovidone (e.g., Kollidon®, Polyplasdone®), povidone K-30, polacrilin potassium, sodium starch glycolate (e.g., Primogel, Explotab®), and the like.

Non-limiting examples of glidants and lubricants includes one or more of stearic acid, magnesium stearate, talc, colloidal silicon dioxide, and sodium stearyl fumarate, and the like.

Non-limiting examples of preservatives includes one or more of phenoxyethanol, parabens such as methyl paraben and propyl paraben and their sodium salts, propylene glycols, sorbates, urea derivatives such as diazolindinyl urea, and the like and mixtures thereof. Non-limiting examples of buffering agents include sodium hydroxide, potassium hydroxide, ammonium hydroxide and the like and mixtures thereof. Non-limiting examples of chelating agents include ethylene diamine tetraacetic acid ("EDTA"), disodium edetate and EDTA derivatives, and the like.

Non-limiting examples of polymers includes one or more of gum arabic, sodium based lignosulfonate, methyl methacrylate, methacrylate copolymers, isobutyl methacrylate, ethylene glycol dimethacrylate, and the like.

Non-limiting examples of gelling agents/viscosifying agents includes one or more of carbomers (carbopol), modified cellulose derivatives, naturally-occurring, synthetic or semi-synthetic gums such as xanthan gum, acacia and tragacanth, sodium alginate, gelatin, modified starches, cellulosic polymers such as hydroxypropyl cellulose, hydroxyethyl cellulose, hydroxypropyl methylcellulose, hydroxypropyl methylcellulose phthalate, and methyl cellulose; co-polymers such as those formed between maleic anhydride and methyl vinyl ether, colloidal silica and methacrylate derivatives, polyethylene oxides, polyoxyethylene-polyoxypropylene copolymers, polyvinyl alcohol and the like.

Non-limiting examples of co-solvents includes one or more of propylene glycol, polyol esters of fatty acids, trialkyl citrate esters, propylene carbonate, dimethylisosorbide, ethyl lactate, N-methylpyrrolidones, transcutol, glycofurol, decaglycerol mono-, dioleate (Caprol PGE-860), triglycerol monooleate (Caprol 3GO), polyglycerol oleate (Caprol MPGO), mixed diesters of Caprylic/Capric acid and propylene glycol (Captex 200), glyceryl mono- and dicaprate (Capmul MCM), isostearyl isostearate, oleic acid, peppermint oil, oleic acid, soybean oil, safflower oil, corn oil, olive oil, cottonseed oil, arachis oil, sunflower seed oil, palm oil, rapeseed oil, ethyl oleate, glyceryl monooleate, Vitamin E TPGS and the like.

Non-limiting examples of solvents includes one or more of water; tetrahydrofuran; propylene glycol; liquid petrolatum; ether; petroleum ether; alcohols, e.g., methanol, ethanol, isopropyl alcohol and higher alcohols; alkanes, e.g., pentane, hexane and heptane; ketones, e.g., acetone and methyl ethyl ketone; chlorinated hydrocarbons, e.g., chloroform, carbon tetrachloride, methylene chloride and ethylene dichloride; acetates, e.g., ethyl acetate; lipids, e.g., isopropyl myristate, diisopropyl adipate and mineral oil and the like.

In an embodiment, the present invention also relates to a pharmaceutical composition that includes: a nanoparticulate formulation comprising particles of Compound I or its salt and a surface stabilizer and a pharmaceutically acceptable excipient, said formulation having an effective average particle size in the range from about 20 nm to about 1000 nm.

In an embodiment, the present invention also relates to a pharmaceutical composition that includes a nanoparticulate formulation comprising particles of Compound I or its salt and a surface stabilizer and a pharmaceutically acceptable excipient, said formulation having an effective average particle size in the range from about 30 nm to about 800 nm or from about 50 nm to about 600 nm.

In an embodiment, the present invention also relates to a pharmaceutical composition that includes a nanoparticulate formulation comprising particles of Compound I or its salt and a surface stabilizer and a pharmaceutically acceptable excipient, said formulation having an effective average particle size in the range from about 70 nm to about 500 nm or from about 100 nm to about 400 nm.

The nanoparticulate formulation of the present invention can be administered as such, or alternately, it can be further converted into a suitable pharmaceutical composition such as solid, liquid or semi-solid preparation for ease of administration. The nanoparticulate formulation or its pharmaceutical composition can be administered by appropriate route which includes, but is not limited to, oral, pulmonary, rectal, ophthalmic, parenteral, intravaginal, local, buccal, nasal or topical route. Preferably, the nanoparticulate formulation or its pharmaceutical composition of the present invention is suitable for oral administration.

In one embodiment the present invention relates to a pharmaceutical composition comprising the nanoparticulate formulation of the invention and a pharmaceutically acceptable excipient wherein the composition is an immediate release composition suitable for oral administration.

In one embodiment the present invention relates to a pharmaceutical composition comprising the nanoparticulate formulation of the invention and a pharmaceutically acceptable excipient wherein the composition is an extended release or a delayed release composition suitable for oral administration.

In one embodiment the present invention relates to a process for preparation of a nanoparticulate formulation. The typical processes involved in the preparation of the nanoparticulate formulation (or pharmaceutical composition containing the nanoparticulate formulation) include various unit operations such as milling, micronization, mixing, homogenizing, sifting, spraying, solubilizing, dispersing, granulating, lubricating, compressing, coating, filling, and the like. These processes, as contemplated by a person skilled in the formulation art, have been incorporated herein for preparing the nanoparticulate pharmaceutical composition of the present invention. The reduction of the particle size may be achieved using various techniques like dry/wet milling, micronization, high pressure homogenization, controlled precipitation using antisolvent, microfluidization and supercritical fluid technology.

In one embodiment the present invention relates to a process for preparation of a nanoparticulate formulation comprising Compound I or its salt and a surface stabilizer, the process comprising the steps of:

a) mixing Compound I or its salt with the surface stabilizer to form a mixture; and;

b) reducing the particle size of the mixture.

In yet another embodiment the present invention relates to a process for preparation of a nanoparticulate formulation comprising Compound I or its salt and a surface stabilizer, the process comprising the steps of:

a) reducing the particle size of the Compound I or its salt; and;

b) mixing said Compound I or its salt with the surface stabilizer.

The present invention also relates to a method of treating a respiratory disorder or pain in a subject, the method comprising administering to the subject the therapeutically effective amount of a nanoparticulate formulation (or pharmaceutical composition containing the nanoparticulate formulation) as described herein.

The term "treating" or "treatment" as used herein also covers the prophylaxis, mitigation, prevention, amelioration, or suppression of a disorder modulated by the TRPA1 antagonist in a subject.

The term "effective amount" or "therapeutically effective amount" denotes an amount of an active ingredient that, when administered to a subject for treating a state, disorder or condition, produces an intended therapeutic benefit in a subject.

The term "subject" includes mammals like human and other animals, such as domestic animals (e.g., household pets including cats and dogs) and non-domestic animals (such as wildlife). Preferably, the subject is a human.

By the term "respiratory disorder" it is meant any condition or disease related to respiration or the respiratory system and includes but is not limited to airway inflammation, asthma, emphysema, bronchitis, COPD, sinusitis, rhinitis, cough, respiratory depression, reactive airways dysfunction syndrome (RADS), acute respiratory distress syndrome (ARDS), irritant induced asthma, occupational asthma, sensory hyper-reactivity, multiple chemical sensitivity, and aid in smoking cessation therapy.

The term "pain" as used herein includes but is not limited to acute pain, chronic pain, mild pain, moderate pain, severe pain, complex regional pain syndrome, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, inflammatory disorders, oesophagitis, gastroeosophagal reflux disorder (GERD), irritable bowel syndrome, inflammatory bowel disease, pelvic hypersensitivity, urinary incontinence, cystitis, stomach duodenal ulcer, muscle pain, pain due to colicky and referred pain.

In one embodiment the present invention relates to use of Compound I or its salt and a surface stabilizer in the preparation of a nanoparticulate formulation for treatment of a respiratory disorder or pain in a subject, said formulation having an effective average particle size in the range from about 20 nm to about 1000 nm.

In aspect of this embodiment, the effective average particle size is in the range from about 30 nm to about 800 nm or from about 50 nm to 600 nm.

In another aspect of this embodiment the effective average particle size is in the range from about 70 nm to about 500 nm or from about 100 nm to 400 nm.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

The following examples are provided to enable one skilled in the art to practice the invention and are merely illustrative of the invention. The examples should not be read as limiting the scope of the invention.

EXAMPLES

Example 1: Nanoparticulate Formulation Comprising Compound I Potassium Salt and Surface Stabilizer

| Ingredients | Composition (% w/w) |
|---|---|
| Compound I Potassium salt | 3.85 |
| Copovidone (Kollidon VA 64) | 15.38 |
| Sodium lauryl sulfate | 7.69 |
| Poloxamer 407 | 3.85 |
| Purified water | q.s. |

Manufacturing Process:

1. Copovidone was dissolved in Purified water under stirring to get a solution.
2. Sodium lauryl sulfate and Poloxamer 407 were dissolved in the solution of step 1 under stirring.
3. Compound I Potassium salt was dispersed in the solution of step 2 under stirring for 15 min, followed by sonication for 45 min.
4. The dispersion of step 3 was homogenized for 3 hrs and soaked for overnight.
5. The dispersion of step 4 was subjected to high pressure homogenization at a pressure between 10,000 to 15,000 psi for 10 cycles.

Particle Size Data of Example 1:

| | Particle size (nm) | | |
|---|---|---|---|
| Time | $D_{10}$ | $D_{50}$ | $D_{80}$ |
| 0 (Initial) | 75 | 135 | 232 |
| 24 hours | 75 | 137 | 239 |

The particle size of the compound I Potassium salt was determined in water using Mastersizer 2000 (Malvern® Instruments Ltd., Malvern, United Kingdom). Three readings were taken for each measurement, and the average size was reported.

Example 2: Pharmaceutical Composition Comprising the Nanoparticulate Formulation of Example 1

| Ingredients | Composition (% w/w) |
|---|---|
| Nanoparticulate formulation of Example 1 | 30.77* |
| Sugar spheres (#120-#140) | 69.23 |
| Total | 100 |

*based on solid contents

Manufacturing Process:

1. The nanoparticulate formulation of Example 1 was loaded onto the Sugar spheres (#120-#140 fraction) using bottom spray technique in Glatt.
2. The granules/beads obtained were assayed.

The pharmaceutical composition was subjected to accelerated stability studies at a temperature of 40° C.±2° C. and relative humidity of 75%±5% for a period of 1 month. The drug assay was performed and active contents were analyzed using HPLC technique. In-vitro dissolution studies were performed using USP type II (Paddle) apparatus in 900 ml od 0.1N HCl as the Dissolution Medium at a temperature of 37±0.5° C. and a speed of 50 revolutions per minute (RPM) for a period of 60 minutes. The aliquots taken out at 60 min were analyzed for active content by HPLC technique. The HPLC parameters include Inertsil ODS 3V, 150×4.6 mm, 5 μm column at a flow rate of 1.0 ml/min, detection wavelength of 265 nm, column temperature of 25° C., Injection volume of 20 μl and Run time of 12 minutes Aqueous orthophosphoric acid buffer (pH 2.5): Acetonitrile in the ratio of 35:65 v/v was used as a mobile phase.

Stability and Dissolution Data for Example 2:

| Time | Assay (%) | % Drug dissolved after 60 minutes |
|---|---|---|
| Initial | 98.5 | 74.2 |
| 1 month/40° C./75% RH | 98.8 | 77.4 |

Example 3: Nanoparticulate Formulation Comprising Compound I Potassium Salt and Surface Stabilizer

| Ingredients | Composition (% w/w) |
|---|---|
| Compound I Potassium salt | 10 |
| Copovidone (Kollidon VA 64) | 40 |
| PEG 4000 | 10 |
| Poloxamer 407 | 10 |
| Purified water | q.s. |

The formulation was prepared by a process as given in Example 1.

Particle Size Data of Example 3:

| | Particle size (nm) | |
|---|---|---|
| Time | $D_{10}$ | $D_{50}$ |
| 0 (Initial) | 78 | 191 |

Example 4: Nanoparticulate Formulation Comprising Compound I Potassium Salt and Surface Stabilizer

| Ingredients | Composition (% w/w) |
|---|---|
| Compound I Potassium salt | 10 |
| Copovidone (Kollidon VA 64) | 40 |
| PEG 4000 | 10 |
| Poloxamer 407 | 10 |
| Vitamin E TPGS | 10 |
| Purified water | q.s. |

The formulation was prepared by a process as given in Example 1.

Particle Size Data of Example 4:

| Time | Particle size (nm) | | |
|---|---|---|---|
| | $D_{10}$ | $D_{50}$ | $D_{80}$ |
| 0 (Initial) | 75 | 174 | 810 |

Example 5: Granules Composition of Nanoparticulate Formulation Comprising Compound I Potassium Salt and Surface Stabilizer

| Ingredients | Composition (% w/w) |
|---|---|
| Microcrystalline Cellulose spheres | 38.1 |
| Compound I Potassium salt | 9.52 |
| Copovidone | 38.1 |
| Sodium lauryl sulfate | 4.76 |
| Poloxamer 407 | 9.52 |
| Purified water | q.s. |
| Total Weight | 100 |

Manufacturing Process:

1. Copovidone, Poloxamer 407 and sodium lauryl sulphate were dissolved into water under stirring to get a solution.
2. Compound I Potassium salt was dispersed into the solution of step 1 under stirring to form uniform suspension.
3. The suspension in step 2 was homogenized using high pressure homogenizer till the desired particle size distribution is obtained.
4. The homogenized suspension in step 3 was loaded on microcrystalline cellulose using glatt bottom spray to form granules.

Particle Size Data of Example 5:

| Time | Particle size (nm) | | | |
|---|---|---|---|---|
| | $D_{10}$ | $D_{50}$ | $D_{80}$ | $D_{90}$ |
| 0 (Initial) | 70 | 126 | 187 | 239 |

Example 6: Stability Data of Granules of Nanoparticulate Formulation Comprising Compound I Potassium Salt after Reconstitution 52 g of granules of Example 5 were reconstituted with 100 ml of water on Day 1, Day 2 and Day 5 and drug content assay was carried out using the dispersion.

| Time | Initial | Day 1 | Day 2 | Day 5 |
|---|---|---|---|---|
| Drug content (%) | 102.8 | 101.8 | 101.3 | 102.2 |

The dispersion was filtered through Whatmann 40 filter to remove microcrystalline spheres the particle size of the filtered nanodispersion was determined.

| Time | Particle size (nm) of nanodispersion formed after reconstitution of granules | | | |
|---|---|---|---|---|
| | $D_{10}$ | $D_{50}$ | $D_{80}$ | $D_{90}$ |
| 0 (Initial) | 67 | 131 | 210 | 279 |

Example 7: Tablet Composition of Nanoparticulate Formulation Comprising Compound I Potassium Salt and Surface Stabilizer

| Ingredients | Composition (% w/w) |
|---|---|
| Drug loaded granules of Example 5 | 65.76 |
| Silica colloidal anhydrous | 0.647 |
| Sodium hydrogen carbonate | 5.177 |
| Microcrystalline cellulose | 18.38 |
| Croscarmellose sodium | 6.47 |
| Sodium steryl fumarate | 0.647 |
| Opadry II 85F18422 (White) | 2.912 |
| Purified water* | q.s. |
| Total Weight | 100 |

*Does not appear in finished product

Manufacturing Process:

1. Drug loaded granules of Example 5, Silica colloidal anhydrous, Sodium hydrogen carbonate, Microcrystalline cellulose were sifted through 40# sieve and were blended together.
2. Croscarmellose sodium was added to blend of step 1 and mixed well.
3. Sodium stearyl fumarate was added to blend of step 2 and mixed well.
4. Lubricated blend of step 3 was compressed using suitable tooling on table compression machine.
5. Tablets of step 4 were coated using aqueous opadry coating solution.
6. Coated tablets of step 5 were packed in HDPE container/Alu-Alu strip/blister.

Example 8: Stability Data of Composition of Nanoparticulate Formulation Comprising Compound I Potassium Salt Tablet compositions of Example 7 were subjected to real time as well as accelerated stability studies. The samples were analyzed for drug content, impurities and in-vitro dissolution.

| Time | Amount of drug (%) dissolved in 45 minutes | % Total impurities (NMT 2%) | Drug content (%) |
|---|---|---|---|
| Real time stability studies on storage at temperature 25° C. ± 2° C. and Relative humidity of 60% ± 5% | | | |
| Initial | 69 | 0.08 | 100.3 |
| 3 months | 68 | 0.24 | 97.6 |
| 6 months | 81 | 0.24 | 100.0 |
| 12 months | 68 | 0.1 | 100.1 |

-continued

| Time | Amount of drug (%) dissolved in 45 minutes | % Total impurities (NMT 2%) | Drug content (%) |
|---|---|---|---|
| Accelerated stability studies on storage at temperature 40° C. ± 2° C. and Relative humidity of 75% ± 5% | | | |
| Initial | 69 | 0.08 | 100.3 |
| 3 months | 68 | 0.16 | 97.9 |
| 6 months | 80 | 0.15 | 99.3 |

Example 9: Determination of Particle Size of Nanoparticulate Formulation in a Pharmaceutical Composition (e.g., Tablet or Capsule)

The tablet containing the nanoparticulate formulation is crushed to get a powder mass. The powder mass can be further subjected to Hot-stage Optical Microscopy technique as described in Yin et. al., Journal of Pharmaceutical Sciences Vol. 94 No. 7, July 2005. Briefly, the powder mass is mounted on the slide, which is heated at controlled rate (e.g., 10° C./min). The particles remaining at higher temperature are confirmed by DSC and variable-temperature powder X-ray diffraction to be crystalline drug particles.

Alternatively, the particle size of the nanoparticulate formulation in a tablet can also be determined by dispersing tablet in a suitable solvent in which the excipients are highly soluble as against the nanoparticulate formulation such that the nanoparticulate formulation remains in dispersed form. Further, the particle size of the dispersion can be determined by the methods as described above.

In another method, particle size of Compound I potassium salt nanodispersion in the pharmaceutical composition can be determined using PXRD peak broadening technique, followed by applying the Scherrer equation $T=K\lambda/\beta\tau \cos \theta$ where $\tau$ is the mean particle dimension, K is a constant of 0.9, $\lambda$ is the X-ray wavelength, $\beta\tau$ is the peak broadening value due to crystal size reduction i.e., the full-width-at-half-maximal (FWHM) difference in radian at a certain Bragg angle ($\Theta$), between a nanoparticulate dispersion and the micronsized excipients. (Ref: Dantuluri A. et. al., Sciforum e-conference ECPS 2011 Communication.)

Further, different imaging techniques or methodologies can be used to expose the particulate formulation contained in pharmaceutical compositions (e.g., tablet), wherein is-situ particle size measurements can be done. Several methods exist which are able to determine the particle sizes in a matrix, like Raman spectroscopy, Transmission Electron Microscopy (TEM), Time of Flight Secondary Ion Mass Spectroscopy (TOF-SIMS), FTIR and NIR microscopy and micro-thermal analysis (μTA).

Although the invention herein has been described with reference to particular embodiments, it is to be understood that these embodiments are merely illustrative of the principles and application of the present invention. It is therefore to be understood that numerous modifications may be made to the illustrative embodiments.

All publications, patents, and patent applications cited in this application are herein incorporated by reference to the same extent as if each individual publication, patent, or patent application was specifically and individually indicated to be incorporated herein by reference.

We claim:

1. A nanoparticulate formulation comprising a single active ingredient, which is a compound N-{4-[2,4-difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide ("Compound I") potassium salt, copovidone, sodium lauryl sulphate or polyethylene glycol and poloxamer, wherein Compound I potassium salt, copovidone, sodium lauryl sulphate or polyethylene glycol and poloxamer are present in a weight ratio of about 1:4:0.5:1, said formulation having an effective average particle size in the range from about 70 nm to about 500 nm.

2. The formulation according to claim 1, wherein the formulation is in the form of a dispersion, liquid suspension, semi-solid suspension or powder.

3. A pharmaceutical composition comprising the nanoparticulate formulation according to claim 1, and a pharmaceutically acceptable excipient.

4. The pharmaceutical composition according to claim 3, wherein the composition is suitable for oral administration.

5. The formulation according to claim 1, wherein the effective average particle size is in the range from about 100 nm to about 400 nm.

* * * * *